US006741887B1

(12) United States Patent
Gleeson

(10) Patent No.: US 6,741,887 B1
(45) Date of Patent: May 25, 2004

(54) APPARATUS AND METHOD FOR PRESENTING PERIODIC DATA

(75) Inventor: Thomas J. Gleeson, St. Louis Park, MN (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 278 days.

(21) Appl. No.: 09/728,640

(22) Filed: Dec. 1, 2000

(51) Int. Cl.⁷ .............................. A61B 5/04; G09G 5/00
(52) U.S. Cl. .................................... 600/523; 345/6
(58) Field of Search ................. 600/108, 509, 600/522, 523, 481, 483; 345/1.1, 1.2, 3.1, 4, 5, 6; 128/916, 920, 922

(56) References Cited

U.S. PATENT DOCUMENTS

| | | | |
|---|---|---|---|
| 4,967,760 A | * 11/1990 | Bennett et al. | 600/528 |
| 5,042,522 A | 8/1991 | Corenman et al. | 137/239 |
| 5,063,275 A | 11/1991 | Rosenfeld et al. | 250/343 |
| 5,159,934 A | 11/1992 | Hoberman | 128/719 |
| 5,296,706 A | 3/1994 | Braig et al. | 250/339 |
| 5,782,773 A | 7/1998 | Kuo et al. | 600/523 |
| 5,830,150 A | * 11/1998 | Palmer et al. | 600/523 |
| 5,931,161 A | 8/1999 | Keilbach et al. | 128/204.22 |
| 5,932,877 A | 8/1999 | Braig et al. | |
| 5,957,855 A | * 9/1999 | Oriol et al. | 600/511 |
| 6,230,048 B1 | * 5/2001 | Selvester et al. | 600/523 |

OTHER PUBLICATIONS

Marquette Medical Systems, "*When the Cost of Uncertainity Is Too Great , ST Guard* ™*cardiac review station,*" 1995, 8 pgs., Marquette Electronics, Inc., U.S.A.
Marquette Medical System, "*QT Guard, a sophisticated analysis system for performing QT measurements,*" 1998, 2 pgs., Marquette Medical Systems, Inc., U.S.A.
Marquette Medical Systems, "*Marquette's Waterfall Display—Quick, confident ST segment assessment,*" 1998, 2 pgs., Marquette Medical Systems, Inc., U.S.A.
U.S. patent application Ser. No. 09/186,310, Werner et al.

* cited by examiner

*Primary Examiner*—Sang Paik
(74) *Attorney, Agent, or Firm*—Foley & Lardner

(57) ABSTRACT

A method and apparatus for graphically presenting periodic data is disclosed herein. One embodiment includes generating a surface based on the periodic data, the contour of the surface corresponding to the amplitudes of the plurality of data points. At least one area of the surface can be visually differentiated from another area of the surface. A rendering mode, viewing orientation, and/or an area of interest associated with the surface can be prescribed and updated in real-time or quasi real-time.

52 Claims, 4 Drawing Sheets

(3 of 4 Drawing Sheet(s) Filed in Color)

APPARATUS AND METHOD FOR PRESENTING PERIODIC DATA

BACKGROUND OF THE INVENTION

The present invention relates generally to displaying periodic data. More particularly, the present invention relates to displaying physiological patient data in such a manner as to facilitate identification of patterns and/or diagnosis of abnormalities.

Medical patient monitors are typically employed to provide a variety of physiological patient data to physicians or other health care providers. Such physiological patient data facilitates diagnosis of abnormalities (such as in emergency rooms), the patient's current condition (such as in operating rooms or in intensive care units), or permit long-term trend monitoring (such as Holter monitoring or stress testing as part of an annual physical examination).

Presently, one or more sensors (also referred to as transducers) are connected to the patient to acquire various physiological information associated with that patient (e.g., electrical impulses, resistance measurements, etc.). Such physiological information is then processed by the medical patient monitors into physiological data suitable for outputting to the physician or other health care provider. The physiological data can be displayed on a screen or provided on paper in either graphical and/or numerical format. Analog or digital strip chart recorders, spreadsheets and plotting programs are examples of output devices of physiological data. Additionally, the physiological data may be stored in a memory device or transmitted over a network for remote access and/or further processing.

In order to present a periodic data parameter over a long interval of time in a diagnostically meaningful manner, such data is preferably presented in graphical format and takes advantage of the periodicity of such data to facilitate the identification of abnormalities or deviations therein. For example, physiological data relating to cardiac cycles are typically shown in graphical format (e.g., as waveforms). Each cardiac cycle, or a portion thereof, may be displayed in a separate two-dimensional plot or graph such that after an interval of time, the display screen may be filed with a plurality of two-dimensional plots. Alternatively, successive waveforms may be presented proximate to each other in one plot or graph. In either case, the graphical display aids in identification of gradual or subtle changes in the data (e.g., waveform morphology) by the physician or health care provider.

Unfortunately, in order to present a large quantity of physiological data in a single screen in a meaningful manner, data presentation may be presented in less than intuitive fashion (e.g., replacing amplitude geometry with color indexing) and for some aspect of the data deemed to be "unimportant", such data may be omitted or otherwise modified. Some users of the equipment find such display representation to be visually unappealing and may result in slowing down or degrading the clinical usefulness of the acquired data. Moreover, once display of the data has been initiated, users usually have limited ability to interface or manipulate the displayed data to further facilitate the clinical usefulness of the data for that particular user.

Thus, there is a need for an apparatus and method for displaying a large amount of periodic data over successive intervals in a compact form without sacrificing data fidelity. There is a further need for an apparatus and method for presenting periodic data over successive intervals in a clinically useful format. There is still a further need for an apparatus and method for interfacing with presented periodic data to facilitate a user's utility of same.

BRIEF SUMMARY OF THE INVENTION

One exemplary embodiment relates to a method of graphically presenting periodic data including a plurality of data points in each time period. Each data point represents an amplitude as a function of time. The method includes generating a surface based on the periodic data. The surface corresponds to the amplitudes of the data points. The method further includes optionally assigning a visually differentiating rendering to at least one area of the surface with respect to an another area of the surface. The method still further includes presenting the surface with the optionally assigned visually differentiating rendering to an output device.

Another exemplary embodiment relates to an apparatus for graphically presenting periodic data including a plurality of data points in each time period. Each data point representing an amplitude as a function of time. The apparatus includes a processor configured to generate a surface based on the periodic data and optionally assign a visually differentiating rendering to at least one area of the surface with respect to an another area of the surface. The apparatus further includes an output device coupled to the processor and configured to present the surface with the optionally assigned visually differentiating rendering. The contour of the surface corresponds to the amplitudes of the data points.

Still another exemplary embodiment relates to an apparatus for graphically presenting periodic data including a plurality of data points in each time period. Each data point representing an amplitude as a function of time. The apparatus includes means for generating a surface based on the periodic data. The surface is representative of the amplitudes of the plurality of data points. The apparatus further includes means for optionally differentiating at least one area of the surface with respect to an another area of the surface. The apparatus still further includes means for presenting the surface for visualization.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The preferred embodiment will become more fully understood from the following detailed description, taken in conjunction with the accompanying drawings, wherein like reference numerals denote like elements, in which.

DETAILED DESCRIPTION OF THE EXEMPLARY EMBODIMENTS

Figure 1:
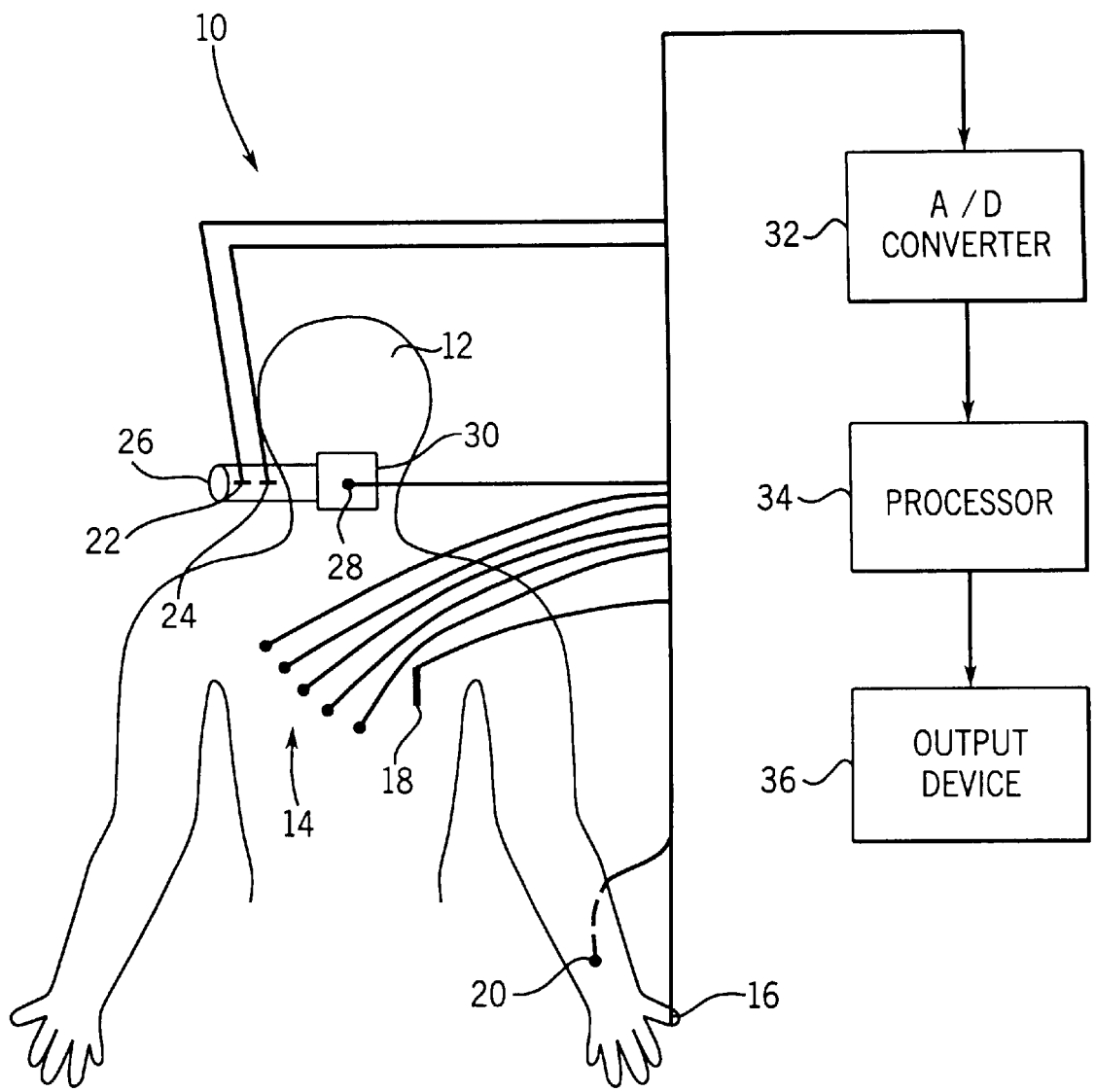
FIG. 1 is a block diagram of a patient monitoring system which employs an embodiment of the present invention.

Referring to FIG. 1, there is shown the major components of a patient monitoring system 10. System 10 includes electrodes 14, an oximetry sensor 16, a catheter 18, an arterial canula 20, a flow meter 22, a pressure sensor 24, an endotrachial tube 26, mask sensors 28, a mask 30, an analog-to-digital (A/D) converter 32, a processor 34, and an output device 36. System 10 is configured to acquire physiological data associated with a patient 12 and to process such data for output to a user of the system (e.g., a physician, a technician, other health care providers, etc.). In this manner, system 10 is configured for use in a variety of clinical environments, including those for conducting long-term trend monitoring such as Holter monitoring or stress testing.

It should be understood that although the following discussion will be directed to electrocardiogram (ECG) data, this is for illustration purposes only and in no way limits the applicability of the embodiments of the present invention to other types of physiological data, such as electroencephalograms (EEGs), Holter, or blood gas concentration levels during cardiac cycles. Moreover, it should also be understood that system 10 may be configured to monitor non-biological entities or specimens and correspondingly output data other than physiological data. Periodic waveform type data in relatively large quantities can benefit from the output capabilities of system 10. Periodic waveform type data refers to data that comprises a plurality of data points for each time period or interval, and which could be modeled as a surface when data corresponding to successive periods or intervals are plotted in a single plot or graph. System 10 preserves data fidelity and presents such data in such a manner as to facilitate identification of trends, gradual or subtle changes, or abnormalities in the displayed data.

System 10 couples to patient 12 via sensors or transducers, such as electrodes 14, oximetry sensor 16, catheter 18, arterial canula 20, flow meter 22, pressure sensor 24, and mask sensors 28. Electrodes 14 are preferably positioned on the patient's chest to obtain cardiac data (e.g., electrocardiogram and heart rate). Oximetry sensor 16 is positioned on the patient's finger to measure hemoglobin oxygen saturation. Catheter 18 and arterial canula 20 are positioned within the patient's chest and arm, respectively, to measure hemoglobin oxygen saturation in the vena cava of the heart and to measure arterial systolic and diastolic pressures, respectively.

Endotrachial tube 26 is positioned proximate the patient's airway and includes flow meter 22 and pressure sensor 24. Flow meter 22 measures trachial gas flow and pressure sensor 24 measures airway pressure. Mask 50 couples to endotrachial tube 26 and includes mask sensors 46 to measure the volume percentage of oxygen and carbon dioxide ($CO_2$) in the patient's mouth.

Signals acquired by electrodes 14, oximetry sensor 16, catheter 18, arterial canula 20, flow meter 22, pressure sensor 24, and mask sensors 28 (collectively referred to as sensors) are transmitted to A/D converter 32 to be converted from analog to digital format suitable as inputs to processor 34. Processor 34 prepares the received data for output to output device 36. Output device 36 presents the data to be viewed by and/or interfaced with a user of the system (e.g., a physician, a technician, etc.). Output device 36 can be a display (such as a cathode ray tube (CRT), a liquid crystal display (LCD), a touch screen, and a projection display), a plotter, a printer, a memory device or a variety of other output devices. Although not shown, A/D converter 32 may instead comprise a part of processor 34. The composition of the sensors may also be altered depending on the data to be displayed on output device 36.

In an exemplary embodiment, processor 34 processes the physiological data for display on output device 36 that comprises an electronic display. Processor 34 may process the data after data acquisition has been completed. Alternatively, data processing may occur at discrete time periods during data acquisition, e.g., data processing after every 10 seconds of data has been acquired. In still another alternative, data processing may occur in real-time, quasi real-time, or with a fixed time lag after commencement of the data acquisition.

The acquired data is stored in a memory of system 10 (not shown). For physiological data relating to the heart, the memory would store a series of ECG traces, each trace representative of a series of cardiac or heartbeat cycles from a particular lead positioned on patient 12. Each trace comprises a waveform having upward and downward deflections (i.e., of variable amplitude) as a function of time. System 10 typically acquires a large amount of physiological data, and, accordingly, a large number of traces are stored in the memory. For example, system 10 may acquire or collect ten seconds of ECG data at minute intervals for several hours to access a patient's chest pains. In another example, system 10 may acquire or collect ECG data for 48 hours following a heart attack or an operation. Moreover, ECG data acquisition typically generates twelve traces per unit time of data acquisition, a trace for each of the following twelve leads: Lead I, Lead II, Lead III, Lead V1, Lead V2, Lead V3, Lead V4, Lead V5, Lead V6, Lead AVL, Lead AVR, and Lead AVF. Thus, in order to present at least a substantial amount of such data in one showing or screen shot with minimal loss in data fidelity while facilitating identification of pattern shifts, a data visualization scheme is included in system 10.

In one embodiment, the data visualization scheme is configured to present data (in the form of data graphics) from one or more leads on output device 36. Particular leads may be designated as default leads in system 10 or the user may be permitted to specify which data (corresponding to particular leads) should be displayed. For example, data graphics corresponding to Leads I, II, and V5 are typically displayed for cardiac ischemia evaluation.

In any case, processor 34 processes a series of traces of a chosen lead to generate a polygon mesh representative of a 2½ dimensional surface (also referred to as a surface height map). The earliest time indexed trace is positioned closest to the bottom and left side of the screen and each successive time indexed trace would then be positioned slightly above (i.e., toward the top of the screen) and to the right of the previous trace. Alternatively, it should be understood that the traces could be positioned to move toward the bottom and left side of the screen as the time index increases. Although each of the traces represent the waveform of one cardiac cycle from a particular lead, they are not necessarily positioned along the horizontal axis (the x-axis) to be time aligned with the traces positioned above and below it. Instead, the traces are aligned along the x-axis based on a physiologically important (and algorithmically calculated) reference point (i.e., a fiducial point) common to, and possibly unique to, that set of traces. In this manner, the corresponding points along each cardiac cycle are presented visually aligned with each other to permit the user to quickly identify patterns and/or anomalies therein.

The contour of the (top) surface of this polygon mesh is defined by the upward and downward deflections (i.e., the amplitudes) of the set of traces that are positioned as discussed above. Generation of the polygon mesh also includes rendering color or shading to its (top) surface. This rendering provides visual differentiation to a given part of the surface of the polygon mesh relative to its surrounding areas. Processor 34 determines a constant reference value (also referred to as an isoelectric line or baseline) of the amplitude from the traces and then determines deviations from this baseline for all (or certain sampling) data points representative of the traces. Data values of cardiac amplitude data points less than (or negative relative to) the baseline are designated a first color (e.g., blue), greater than (or positive relative to) the baseline are designated a second color (e.g., red), and at or near the baseline are designated a third color (e.g., white). As the deviation from the baseline increases, the intensity of the designated color would also increase. Thus, continuing the example, data points having the greatest deviation in the positive direction relative to the baseline would be intensely red while those having the greatest deviation in the negative direction relative to the baseline would be intensely blue.

Alternatively, the coloring scheme may include more or less than three "base" colors, use any one of a variety of colors as the "base" colors, and/or designate a different color for each incremental deviation from the baseline instead of employing intensity variations from the "base" colors. It is understood that rendering color or shading includes rendering true colors, gray tones, patterns (such as stripes, cross hatching, polka dots, etc.), or other types of rendering to visually differentiate one area from another. It is also contemplated that the user may specify his/her desired colors and/or system 10 may provide default settings.

Preferably, the user selects a rendering mode of the polygon mesh surface prior to the color assignment of the surface, and, more preferably before generation of the polygon mesh commences. The rendering mode of the surface can be selected from: a wire frame mode (see FIG. 2), a vertex colored or height indexed mode (see FIG. 3), a material shaded mode (see FIG. 4), or a combination mode (see FIG. 5). Such rendering is performed in processor 34 and the user inputs his/her desired rendering mode via an input device (not shown) included in system 10. The input device can include, but is not limited to, a mouse, a joystick, a keyboard, a trackball, a touch screen, a light wand, and a voice control device.

Figure 2:
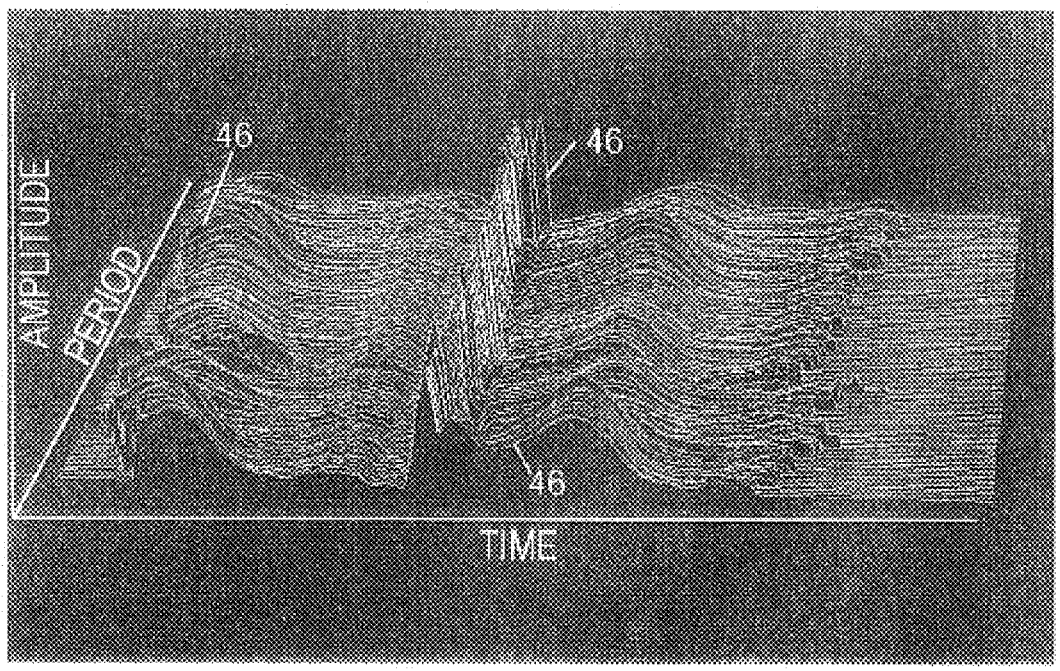
FIG. 2 is a first visualization of physiological data acquired by the patient monitoring system of FIG. 1.

A sample of data graphic or visualization in wire frame mode as presented on output device 36 is shown in FIG. 2. Wire frame mode comprises the individual traces presented as line plots 46. Accordingly, any one trace is discernable from its neighboring traces. Wire frame mode preferably does not include color assignment or coding. However, it is contemplated that in another embodiment, the wire frame mode may include color assignment as a function of amplitude as described above.

Figure 3:
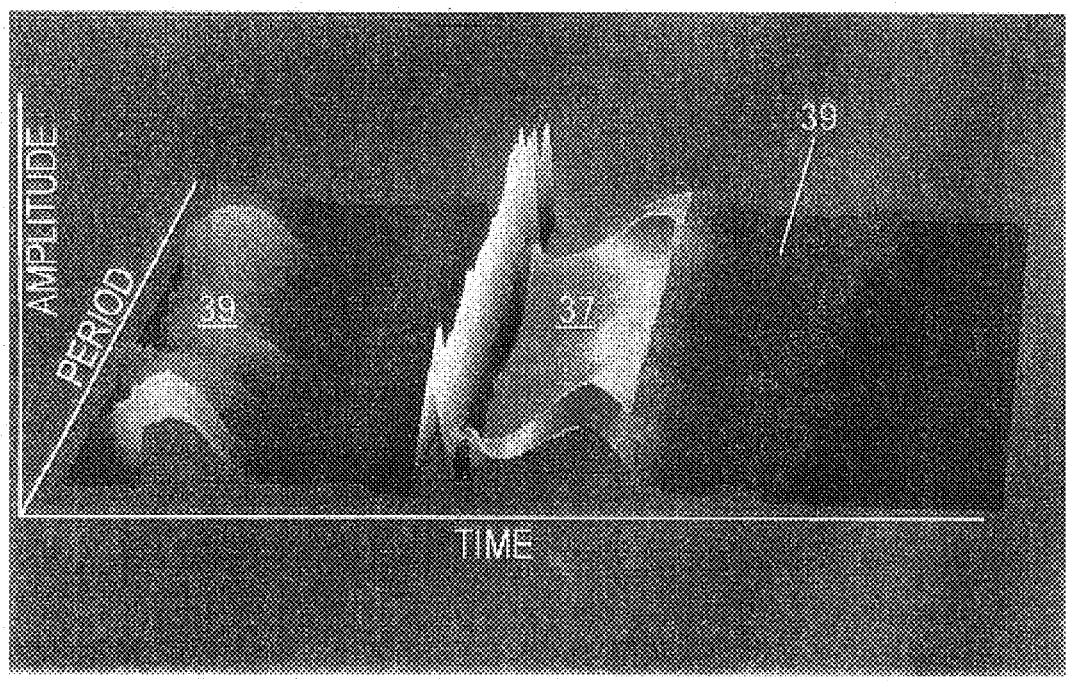
FIG. 3 is a second visualization of physiological data acquired by the patient monitoring system of FIG. 1.
Figure 4:
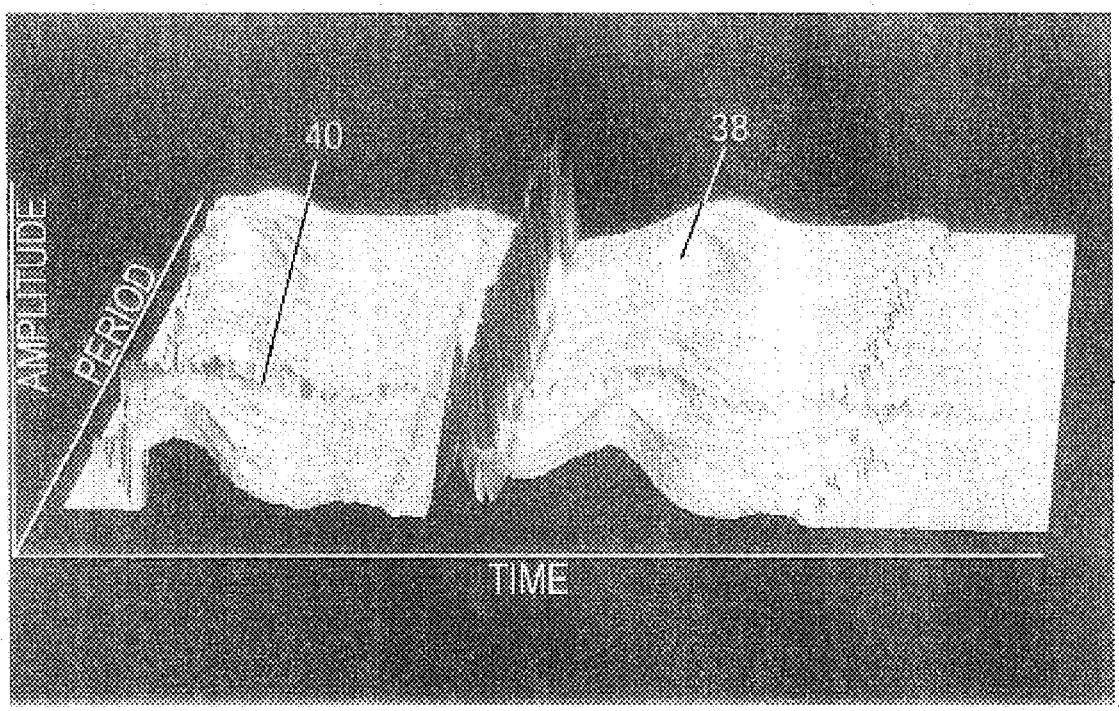
FIG. 4 is a third visualization of physiological data acquired by the patient monitoring system of FIG. 1.
Figure 5:
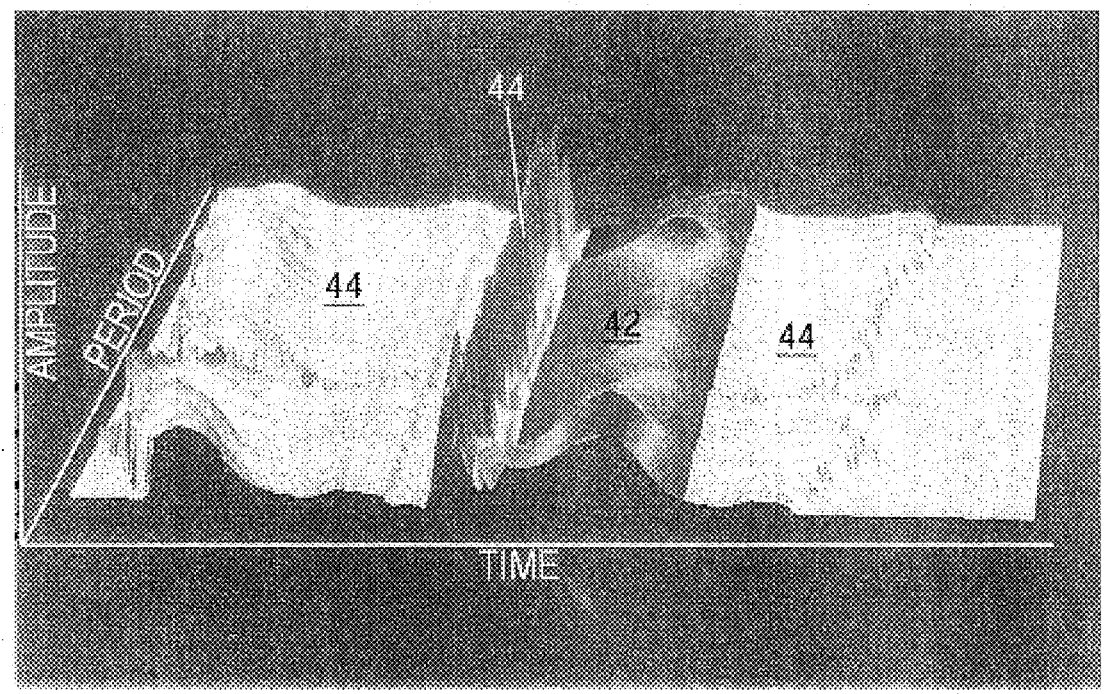
FIG. 5 is a fourth visualization of physiological data acquired by the patient monitoring system of FIG. 1.

Samples of data graphics or visualizations in height indexed, material shaded, and combination modes, as presented on output device 36, are shown in FIGS. 3–5, respectively. Each of these modes includes a (top) surface (the contour a function of the amplitudes of the traces comprising the polygon mesh) that is colored or shaded as described below.

Height indexed mode assigns and renders colors as a function of amplitude to the entire (top) surface, or a portion of the (top) surface (i.e., an area of interest), of the polygon mesh. In FIG. 3, the data graphic in height indexed mode include an area of interest 37 and surrounding areas 39. As can be seen, only area of interest 37 has been color rendered. Such an area of interest is pre-specified by the user or is provided as a default setting by system 10. Area of interest 37 comprises a particular segment of the cardiac cycle in each of the traces comprising the polygon mesh. As an example, area of interest 37 shown in FIG. 3 is the ST segments of the cardiac cycles. The remaining areas of the surface, i.e., surrounding areas 39, are not rendered or may be rendered a neutral color regardless of its actual amplitudes.

Material shaded mode assigns one color to the entire surface. However, the resulting polygon mesh will include color or shade variations (as shown in FIG. 4) due to the particular orientation or direction of the polygon mesh surface with respect to the viewer (more particularly, the viewing angle of the viewer). The surface includes renderings of light and shadow areas (e.g., a light area 38 and a shadow are 40, respectively), much as a surface would be rendered in the presence of directional light from a fixed light source. Such rendering makes it easier to appreciate the contour of the surface and changes from one area to another on the surface.

Combination mode renders the entire surface of the polygon mesh in material shaded mode (as described above) except when an area of interest has been specified. In such a case, combination mode renders an area of interest 42 as a function of amplitude and the remaining surface, i.e., surrounding areas 44, is rendered in material shaded mode (as shown in FIG. 5). Preferably, surrounding areas 44 are in gray tone and area of interest 42 is in color. In FIG. 5, area of interest 42 is the ST segments of the cardiac cycles. Alternatively, area of interest 42 may be other parts of the cardiac cycle, such as the QRS complex.

For modes including an area of interest (e.g., height indexed mode and combination mode), the color range is determined relative to the minimum and maximum amplitudes within the area of interest. As such, there will be color compression, i.e., more colors in a smaller amplitude range, which makes it easier to identify subtle changes or anomalies in the waveforms. Moreover, by controlling the width of the area of interest, the user can further effect color compression, e.g., a smaller width typically corresponds to smaller changes in amplitude.

Once at least a portion of a data graphic is displayed on output device 36, system 10 provides further interactive features to the user. System 10 permits real-time or quasi real-time interaction with the presented data graphic to make it even easier for the user to quickly identify patterns or changes and/or further investigate suspect time periods. For example, system 10 permits the user to change the rendering mode of the current data graphic.

Figure 6:
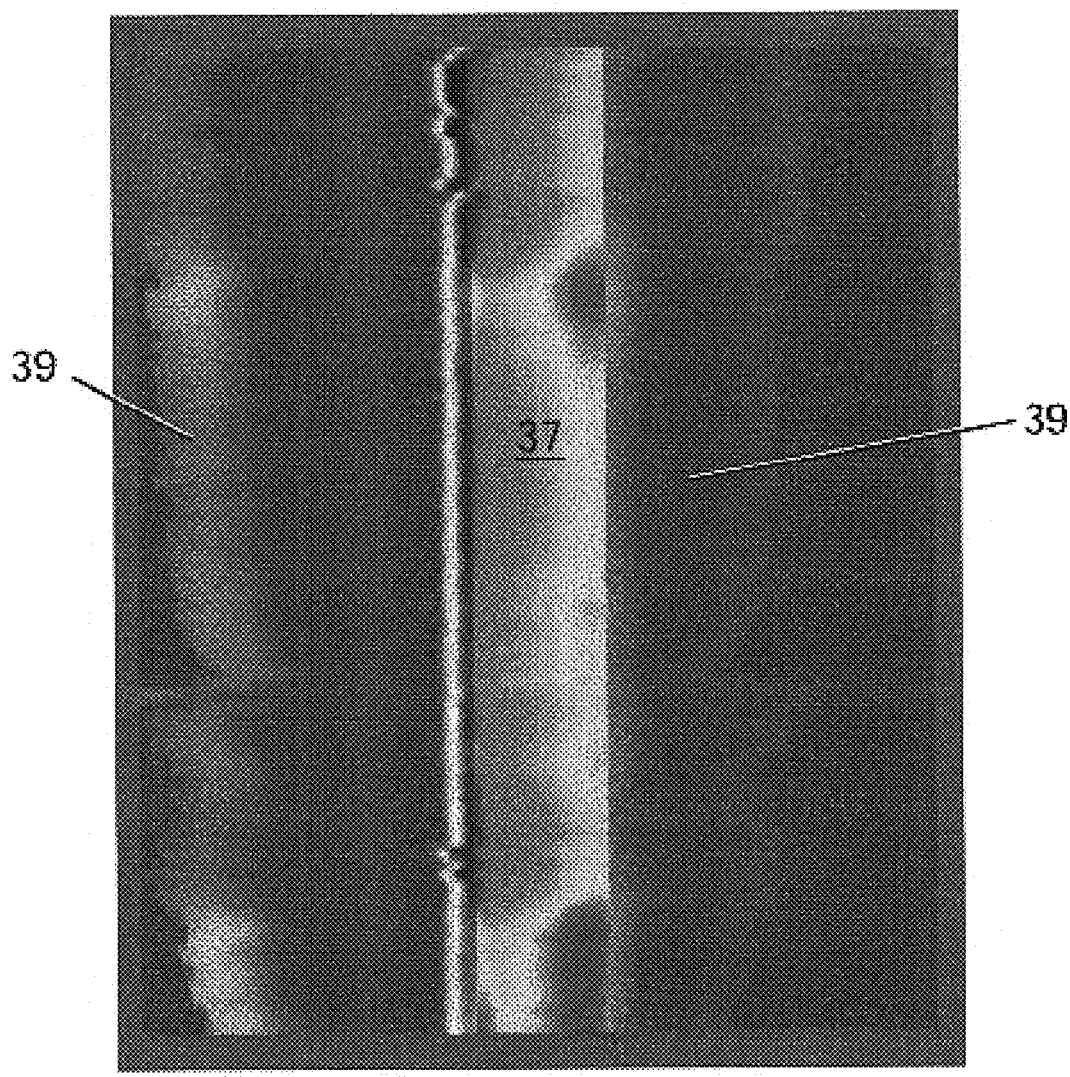
FIG. 6 is a fifth visualization of physiological data acquired by the patient monitoring system of FIG. 1.

In another example, system 10 permits the user to modify the viewing orientation of the polygon mesh. Using the input device included in system 10, the user accesses prescription tools (such as on a graphical user interface), as is well-known in the art, to zoom in/out (e.g., magnification factor), rotate, and/or translate the displayed data graphic. Accordingly, the data graphics of FIGS. 2–5 are oriented such that the viewer is provided with perspective views of the rendered surface (in other words, the viewing direction is from the right of the ST segments). In contrast, the data graphic of FIG. 6 shows a top view of the rendered surface. Specifically, FIG. 6 is a top view of the data graphic of FIG. 3 (i.e., data graphic rendered in height indexed mode with the ST segments as the area of interest) showing area of interest 37 and surrounding areas 39.

Another interactive feature of system 10 is a "sliding window" feature. With respect to the height indexed and combination modes, in addition to being able to initially specify an area of interest for color rendering (such as based on alignment and fiducial points), the user may also change the area of interest by specifying an area to the left or right of the current area of interest (i.e., to render a different segment of the cardiac cycle). This is somewhat analogous to sliding a viewing window to the left or right to focus on a different segment of the cardiac cycle. Furthermore, as discussed above, system 10 may also permit the user to specify the width of the viewing window (i.e., the time period within the cardiac cycle to be rendered).

In this manner, a large amount of data is visually presented in such a way as to facilitate identification of data patterns, changes, and/or anomalies for diagnostic and therapeutic purposes. The data presentation scheme of the present invention preserves waveform morphology and provides rendering options, such as perspective contoured surfaces representative of waveform deflections for intuitive display of data. Moreover, the data presentation scheme permits prescriptive modification of the displayed data, to tailor the data presentation for any given viewer of the data and/or to better focus in on suspect time periods within the data. As such, for example, cardiac ischemia can be investigated by focusing on the occurrence of an elevated region in the ST segments of the cardiac cycles.

While the embodiments and application of the invention illustrated in the figures and described above are presently preferred, it should be understood that these embodiments are offered by way of example only. For example, output device 36 may display more than one data graphic at a given time, one data graphic for each of, such as, Leads I, II, and V5. Each of the data graphics may have a different rendering mode, viewing angle/orientation, color scheme, etc., from each other. In another example, the coloring scheme for the combination and/or height indexed modes may be based on the maximum and minimum amplitude range of the traces. In still another example, the prescription flexibility described above may be used to specify aspects of the data graphics prior to its initial presentation on output device 36. Accordingly, the present invention is not limited to a particular embodiment, but extends to various modifications that nevertheless fall within the scope of the appended claims.

What is claimed is:

1. A method of graphically presenting periodic data including a plurality of data points in each time period, each data point representing an amplitude as a function of time, comprising:
   generating a surface based on at least two periods of the periodic data, the surface corresponding to the amplitudes of the data points;
   assigning a visually differentiating rendering to at least one area of the surface within a discernable boundary; and
   presenting the surface with the assigned visually differentiating rendering to an output device.

2. The method of claim 1, wherein the periodic data include periodic non-scalar waveforms.

3. The method of claim 1, wherein the periodic data is physiological data.

4. The method of claim 3, wherein the periodic data is selected from a group including electrocardiogram data, electroencephalogram data, Holter data, and blood gas concentration data.

5. The method of claim 1, wherein generating a surface includes aligning successive sets of data points based on a fiducial point, the periodicity of the periodic data determining each set of data points.

6. The method of claim 1, wherein the visually differentiating rendering is selected from a group including coloring, gray toning, shading, and patterning.

7. The method of claim 1, further comprising prescribing a rendering mode to specify the areas of the surface to be visually differentiatingly rendered.

8. The method of claim 7, wherein the rendering mode is selected from a group including a wire frame mode, a height indexed mode, a material shaded mode, and a combination mode.

9. The method of claim 8, further comprising prescribing an area of interest to be visually differentiatingly rendered for the height indexed mode or the combination mode.

10. The method of claim 9, wherein prescribing an area of interest includes specifying a width, the width corresponding to a certain segment within the periodicity of the periodic data.

11. The method of claim 9, wherein the visually differentiating rendering of the area of interest includes color compression based on the maximum and minimum amplitudes of the data points comprising the area of interest.

12. The method of claim 7, further comprising prescribing a different rendering mode to the surface presented on the output device.

13. The method of claim 1, further comprising prescribing a viewing orientation of the surface presented on the output device.

14. The method of claim 13, wherein prescribing a viewing orientation includes selecting from a group including a translation, a rotation, and a magnification factor.

15. The method of claim 1, wherein at least one of the generating step, the optionally assigning step, and the presenting step is performed in real-time.

16. The method of claim 1, wherein the surface is a contoured surface.

17. The method of claim 1, wherein the surface is a polygon mesh.

18. An apparatus for graphically presenting periodic data including a plurality of data points in each time period, each data point representing an amplitude as a function of time, comprising:
   a processor configured to generate a surface based on at least two periods of the periodic data and to assign a visually differentiating rendering to at least one selected area of the surface; and
   an output device coupled to the processor and configured to present the surface with the assigned visually differentiating rendering, wherein the surface corresponds to the amplitudes of the data points.

19. The apparatus of claim 18, wherein the periodic data include periodically repeating waveform morphology.

20. The apparatus of claim 18, wherein the periodic data is physiological data.

21. The apparatus of claim 18, wherein the output device is selected from a group including a cathode ray tube (CRT) display, a liquid crystal display (LCD), a touch screen, a projection display, a plotter, a printer, and a memory device.

22. The apparatus of claim 18, wherein the processor is configured to generate the surface by aligning successive sets of data points based on a fiducial point, the periodicity of the periodic data determining each set of data points.

23. The apparatus of claim 18, wherein the visually differentiating rendering is selected from a group including coloring, gray toning, shading, and patterning.

24. The apparatus of claim 18, further comprising an input device coupled to the processor and configured to accept prescription of a rendering mode.

25. The apparatus of claim 24, wherein the rendering mode is selected from a group including a wire frame mode, a height indexed mode, a material shaded mode, and a combination mode.

26. The apparatus of claim 25, wherein the input device is further configured to accept prescription of an area of interest to be visually differentiatingly rendered for the height indexed mode or the combination mode.

27. The apparatus of claim 26, wherein prescription of the area of interest includes specifying a width, the width corresponding to a certain time segment within the periodicity of the periodic data.

28. The apparatus of claim 26, wherein the visually differentiating rendering of the area of interest includes color compression based on the maximum and minimum amplitudes of the data points comprising the area of interest.

29. The apparatus of claim 24, wherein the processor is configured to update the rendering mode of the surface presented on the output device in accordance with each updated rendering mode prescription received by the input device.

30. The apparatus of claim 18, wherein the processor is configured to update a viewing orientation of the surface presented on the output device in accordance with each updated viewing orientation specified by an operator.

31. An apparatus for graphically presenting periodic data including a plurality of data points in each time period, each data point representing an amplitude as a function of time, comprising:
   means for generating a surface based on at least two periods of the periodic data, the surface representative of the amplitudes of the plurality of data points;
   means for differentiating at least one bounded area of the surface; and
   means for presenting the surface for visualization.

32. The apparatus of claim 31, wherein the periodic data is physiological data.

33. The apparatus of claim 31, wherein means for generating includes aligning successive sets of data points based on a fiducial point, the periodicity of the periodic data determining each set of data points.

34. The apparatus of claim 31, wherein the means for optionally differentiating includes visually differentiating using at least one of color, gray tones, shades, and patterns.

35. The apparatus of claim 31, wherein the means for optionally differentiating includes rendering the surface in a mode selected from a wire frame mode, a height indexed mode, a material shaded mode, and a combination mode.

36. The apparatus of claim 35, further comprising means for prescribing an area of interest for the height indexed mode or the combination mode.

37. The apparatus of claim 36, wherein the means for prescribing includes prescribing a width, the width corresponding to a certain time segment within the periodicity of the periodic data.

38. The apparatus of claim 36, further comprising means for compressing the visual differentiating index of the area of interest based on a maximum amplitude and a minimum amplitude of the data points comprising the area of interest.

39. The apparatus of claim 31, further comprising:
   means for updating a rendering mode of the surface presented on the means for presenting; and
   means for updating a viewing orientation of the surface presented on the means for presenting.

40. An apparatus for graphically presenting periodic data to a user as a three dimensional surface having a first axis, a second axis, and a third axis, the periodic data including a plurality of data points in each time period, each data point representing an amplitude as a function of time, the apparatus comprising:
   a processor configured to generate the three dimensional surface, wherein the first axis is representative of time, wherein second axis is representative of period, and the third axis is representative of amplitude, and wherein the processor is further configured to allow the user to select a portion of the surface and assign a visually differentiating rendering to the portion of the surface with respect to an unselected area of the surface; and
   an output device coupled to the processor and configured to present the surface with the assigned visually differentiating rendering, wherein the surface corresponds to the amplitudes of the data points.

41. The apparatus of claim 40, wherein the periodic data include periodically repeating waveform morphology.

42. The apparatus of claim 40, wherein the periodic data is physiological data.

43. The apparatus of claim 40, wherein the output device is selected from a group including a cathode ray tube (CRT) display, a liquid crystal display (LCD), a touch screen, a projection display, a plotter, a printer, and a memory device.

44. The apparatus of claim 40, wherein the processor is configured to generate the surface by aligning successive sets of data points based on a fiducial point, the periodicity of the periodic data determining each set of data points.

45. The apparatus of claim 40, wherein the visually differentiating rendering is selected from a group including coloring, gray toning, shading, and patterning.

46. The apparatus of claim 40, further comprising an input device coupled to the processor and configured to accept prescription of a rendering mode.

47. The apparatus of claim 46, wherein the rendering mode is selected from a group including a wire frame mode, a height indexed mode, a material shaded mode, and a combination mode.

48. The apparatus of claim 47, wherein the input device is further configured to accept prescription of an area of interest to be visually differentiatingly rendered for the height indexed mode or the combination mode.

49. The apparatus of claim 48, wherein prescription of the area of interest includes specifying a width, the width corresponding to a certain time segment within the periodicity of the periodic data.

50. The apparatus of claim 48, wherein the visually differentiating rendering of the area of interest includes color compression based on the maximum and minimum amplitudes of the data points comprising the area of interest.

51. The apparatus of claim 46, wherein the processor is configured to update the rendering mode of the surface presented on the output device in accordance with each updated rendering mode prescription received by the input device.

52. The apparatus of claim 40, wherein the processor is configured to update a viewing orientation of the surface presented on the output device in accordance with each updated viewing orientation specified by the user.

* * * * *